(12) United States Patent
Tester et al.

(10) Patent No.: US 8,142,812 B2
(45) Date of Patent: Mar. 27, 2012

(54) CHEMICAL CARRIER BASED ON A BETA-LIMIT DEXTRIN

(75) Inventors: Richard Frank Tester, Glasgow (GB); Xin Qi, Glasgow (GB)

(73) Assignee: Glycologic Limited, Glasgow (GB)

( * ) Notice: Subject to any disclaimer, the term of this patent is extended or adjusted under 35 U.S.C. 154(b) by 850 days.

(21) Appl. No.: 10/517,558

(22) PCT Filed: Jul. 29, 2003

(86) PCT No.: PCT/EP03/08358
§ 371 (c)(1), (2), (4) Date: Jul. 13, 2005

(87) PCT Pub. No.: WO2004/014156
PCT Pub. Date: Feb. 19, 2004

(65) Prior Publication Data
US 2006/0134006 A1    Jun. 22, 2006

(30) Foreign Application Priority Data
Aug. 2, 2002 (GB) .................................. 0217930.7

(51) Int. Cl.
A61K 9/14 (2006.01)
C13K 1/06 (2006.01)
C08B 30/00 (2006.01)
C12P 19/22 (2006.01)

(52) U.S. Cl. .......... 424/484; 127/40; 536/102; 536/103; 424/488

(52) U.S. Cl. ..............................................................

(58) Field of Classification Search .................. None
See application file for complete search history.

(56) References Cited

U.S. PATENT DOCUMENTS

| | | | | |
|---|---|---|---|---|
| 2,156,810 A * | 5/1939 | Garbutt | .......................... | 426/5 |
| 4,748,032 A * | 5/1988 | Kono et al. | ................... | 426/321 |
| 4,780,149 A * | 10/1988 | Kaper et al. | .................... | 127/38 |
| 5,482,560 A * | 1/1996 | Ammeraal et al. | ............. | 127/40 |
| 5,958,453 A * | 9/1999 | Ohno et al. | ................... | 424/465 |
| 6,046,185 A * | 4/2000 | Burgoyne et al. | ............. | 514/178 |
| 7,132,113 B2 * | 11/2006 | Zerbe et al. | ................... | 424/439 |

FOREIGN PATENT DOCUMENTS
NL    EP 0 242 913 A2 *    4/1987

OTHER PUBLICATIONS

Remington: The Science and Practice of Pharmacy; (1995); p. 710.*
Halls' products webpage (as of 2009); website: http://www.gethalls.com/products.aspx.*
Tester et al. "β-limit dextrin—Properties and applications" Food Hydrocolloids (2011); pp. 1-5.*
http://members.home.nl/ajansma/zetmeel/infoe/chapter2.htm; published Nov. 25, 2001; see p. 4 following Fig. 2.4; downloaded Oct. 4, 2011.*

* cited by examiner

Primary Examiner — Robert A Wax
Assistant Examiner — Jeffrey T Palenik
(74) Attorney, Agent, or Firm — Janet Sleath; Speckman Law Group PLLC (57) ABSTRACT

A formulation, especially a pharmaceutical formulation, comprises an active agent and a carrier for the active agent, wherein the carrier comprises a beta-limit dextrin. The formulation may be a bioadhesive pharmaceutical formulation in which the beta-limit dextrin acts as a mucoadhesive agent. The active agent is a pharmaceutically active agent or a flavour or fragrance which is intended for delivery into the buccal cavity. A use of beta-limit dextrin as a disintegrant, a dispersant, and a mucoadhesive agent is also described. Also described is a nutritional product such as an energy drink which includes beta-limit dextrin as an energy source.

16 Claims, 6 Drawing Sheets

CHEMICAL CARRIER BASED ON A BETA-LIMIT DEXTRIN

TECHNICAL FIELD

The invention relates to solid and fluid formulations comprising an active agent and a carrier for the active agent. This invention also relates to the use of the carrier as a provider of energy in drinks, foods and pharmaceutical preparations.

BACKGROUND ART

Starches are comprised of α-glucans (amylose and amylopectin in variable proportions, amounting to ~82 to 89%), moisture (~11 to 17%), lipids (cereal starches only, <1.5%) and protein (~0.5%) with some α-glucan phosphate-esters (especially in potato amylopectin). Plants produce starches in different sizes and shapes which reflect the botanical origin. In rice starch for example, the granules are <5 μm in diameter while in potato starch they may exceed 50 μm. The amylose fraction of starches comprise predominantly linear α-(1-4)-glucan molecules with a molecular weight of ~0.25 to 0.50 million Daltons. Amylopectin molecules are much larger with a molecular weight of a few million Daltons (probably 8-10 million Daltons) and comprise a heavily branched structure of small unit chains (~15 to 80 glucose units long). The unit chains are like amylose α-(1-4)-glucans (~95% of bonds) but are linked together by α-(1-6) bonds (~5%). Native starch granules contain double helices of amylopectin which associate together to form crystalline laminates which are interspersed with amorphous amylopectin branch regions and amylose chains.

The properties of native starches from different botanical origins may be modified by genetic, chemical, enzymatic and/or physical processing. During the last few centuries, novel mutations have been developed where the ratio of amylose to amylopectin in the starches has been modified to create 'high amylose' starches where the α-glucan fraction may represent >70% amylose (<30% amylopectin) and 'waxy' starches where the amylopectin fraction may represent >70% amylopectin (<30% amylose). Modern methods of 'transgenic' technology may also be used to create novel glucans within starch granules with different chain lengths, distributions and potentially even sugar residues other than glucose. Chemical methods have been used to enhance the properties of starch granules where residues may be added by chemical bonding, stabilisation may be achieved by cross-linking or molecular weight may be reduced by hydrolysis (with for example acids). Glucose syrups may be made from starches by acid hydrolysis but are more often made by enzymatic hydrolysis (below). Here, amylases (specifically α-amylase) and amyloglucosidase can be used to produce syrups with variable proportions of α-dextrins, different chain lengths and sugars (glucose and maltose). Physically, starches may be pre-gelatinised (heated in water to remove crystallinity and dried to make 'instant' products) or damaged (e.g. milled to remove ordered structure) to moderate their functionality also.

Dextrins represent hydrolytic products of starches. They are produced using a number of approaches as discussed above.

Extensive acid hydrolysis may be used to produce low molecular weight dextrins (<degree of polymerisation, DP, ~20) where they may be branched or linear, together with sugars in variable proportions. The extent of hydrolysis is described relative to the amount of reducing power compared to a standard dextrose solution (dextrose equivalent, DE). When glucose syrups are purchased they are defined in terms of DE which suit specific applications. These products are used extensively in the food industry in confectionery, desserts, drinks, cakes and pastries etc. where there is a requirement for sweetness and product 'body'. In the pharmaceutical industry there is a similar need for glucose syrups in for examples pastilles and tinctures with a need for pure glucose (dextrose) in for example intra-venous products.

Less extensive acid hydrolysis of starches (with some transglucosidation and repolymerisation) is achieved by treating dry starches with acids and heating at high temperatures. These dextrin products are described as 'pyrodextrins' which readily disintegrate in water and progressively solubilise. They are classified as 'white', 'yellow' or 'British Gums'. These dextrins have varying disintegrating and solubilising characteristics and have specific applications as for example tablet excipients.

Cyclodextrins are ring forms of dextrin oligomers. The rings may contain six, seven or eight glucose residues forming a hydrophobic core and hydrophilic exterior. Hydrophobic residues (e.g. drugs) may be located inside these cores and provide a vehicle for drug delivery. A number of manufacturers prepare cyclodextrins and their industrial utilisation is quite well established (below).

Unlike the pyrodextrins, α-(limit)-dextrins generated by α-amylase hydrolysis are not employed as high molecular weight products (where there is limited hydrolysis), either in the food or pharmaceutical sectors. Similarly, β-limit dextrins produced by hydrolysis of soluble starches (generating the dextrins from amylopectin and maltose sequentially from the α-glucan non-reducing ends discussed below) are not used extensively in these industries. The α-limit dextrins become more soluble as hydrolysis is extended which, although random, is initially restricted to starch amorphous regions. The β-limit dextrins are highly soluble as exterior chains of amylopectin have been hydrolysed (to maltose) leaving short stubs attached to the (high molecular weight) branched limit-dextrin residues. β-limit dextrins are not at present commercially available in significant quantities.

According to the National Starch web directory, a dextrin may be defined as:

'Dextrins are starch hydrolysis products obtained in a dry roasting process either using starch alone or with trace levels of acid catalyst. The products are characterised by good solubility in water to give stable viscosities. Four types exist: White, Yellow, British Gums and Solution-stable dextrins.'

Note that in reference to this commercially accepted term, citations in patents referring to the use of 'dextrins' (e.g. Gregory (1983) and Gole et al (1994), as discussed below) exclude β-limit dextrins since they can only be produced in the solubilised and not the dry state.

The properties of different dextrins are, as discussed above, very different in terms of their chemical and physical properties. They also have different properties with respect to their potential to be hydrolysed by different enzymes. Comparisons are broadly made as follows:

Comparison of Properties of Different Dextrins

Note that commercial dextrins are produced by heating starches in the presence of a very small amount of acid which induces hydrolysis, transglucosidation and repolymerisation.

| Dextrin | Product characteristics | Chemical properties | Physical properties |
|---|---|---|---|
| β-limit dextrin [Not a dextrin according | White powder produced by hydrolysing | Molecular weight of dextrin ~50% | Soluble powder with no granular or |

-continued

| Dextrin | Product characteristics | Chemical properties | Physical properties |
|---|---|---|---|
| to common commercial/ industrial usage of the term, see definition above] | solubilised amylopectin (from starch) with β-amylase | that of amylopectin. Incorporates no amylose residues. Maltose would be present (from amylose and amylopectin hydrolysis) unless removed by for example dialysis or chromatography. | crystalline form - i.e. amorphous. |
| British Gums [True commercial dextrin] | Dextrin, usually yellow or brown and darker than standard 'yellow dextrins' below. Powder form produced by roasting~dry starch at high temperatures at~neutral pH. | Hydrolysed starches incorporating residues of amylose and amylopectin which will incorporate some transglucosidation and repolymerisation | Dark coloured and relatively soluble - especially when heated - in water. |
| Maltodextrin [Not a dextrin according to common commercial/ industrial usage of the term, see definition above] | Produced from extensive acid or α-amylase (α-limit dextrin) hydrolysis of starch. Component of glucose syrups. | Branched dextrins comprising α-(1-4) and α-(1-6) bonds. Low molecular weight (degree of polymerisation, DP, <~20) soluble branched product. | Soluble dextrins with reducing power much greater than starch polysaccharides but less than free sugars. Dextrose equivalence (DE), 5-20. |
| White Gums [True commercial dextrin] | Dextrin, usually~white. Powder form produced by roasting~dry starch at relatively low temperatures at low pH. | Hydrolysed starches incorporating residues of amylose and amylopectin which will incorporate some transglucosidation and repolymerisation | Light coloured and relatively soluble - especially when heated - in water. |
| Yellow Gums (also referred to as Canary Gums) [True commercial dextrin] | Dextrin, yellow. Powder form produced by roasting~dry starch at relatively high temperatures at low pH. | Highly converted hydrolysed starches incorporating residues of amylose and amylopectin which will incorporate some transglucosidation and repolymerisation | Yellow coloured and relatively soluble - especially when heated - in water. |

Cyclodextrins and their derivatives have been used extensively in pharmaceutical applications and details may be found in a number of patent sources (e.g. Uekama et al, 1989).

As discussed above, amylopectin can be converted to β-limit dextrin by conversion with β-amylase. This enzyme works from the non-reducing end of the amylopectin molecule hydrolysing the exterior (external) chains leaving stubs (G2-G3) attached to the β-limit dextrin. Typically, 50-60% of the amylopectin is hydrolysed in this way (converted to maltose) reducing the molecular weight accordingly (from for example ~8 million Daltons to ~3 million). These products are readily hydrolysed by α-amylase and especially amyloglucosidase to glucose. The amylopectin molecule is sparingly soluble and slowly retrogrades (crystallises) from solution. The β-limit dextrin, is however, highly soluble and would not readily retrograde from solution.

One important application of solid dose formulations is the application in rapid release oral dose (buccal melt) type formulations. These products have been described by Ohno et al (1999) in relation to their buccal type formulations and those of their competitors. The proposed advantage of the Ohno et al (1999) technology over their competitors is the capacity to make solid formulations that might disintegrate rapidly. The technology describes the use of a pharmaceutically active agent, erythritol, crystalline cellulose and a disintegrant.

Fast dissolving formulations have been described by Makino et al (1993) where they describe the use of an active ingredient, a carbohydrate and a barely sufficient amount of water to moisten the surface of particles of the said carbohydrate into a tablet form and a fast dissolving tablet obtained by this method. The carbohydrate fraction is defined as to include sugar, starch-sugars, lactose, honey, sugar alcohols and tetroses with tablets which are porous with excellent digestibility, solubility and adequate strength. It is stated that the carbohydrate to be employed must be 'soluble in water and does not adversely affect the active ingredient (for example, decomposition of the active ingredient)'. The disclosure concentrates on sugars as they would be expected to dissolve and disperse apart from the active ingredients in tablets without entrapment-type interactions upon hydration. The disclosed preference is to use 'sucrose, glucose, maltitol, xylitol, erythritol and so on' [sugar and sugar alcohols but no mention of oligo- or polysaccharides]. Also mentioned are 'sugar, starch-sugars, lactose, honey, sugar-alcohols, tetroses, sucrose, coupling-sugars, fructooligosaccharides, palatinose and so on'. Sugars are elaborated as 'glucose, maltose, powdered syrup, starch syrup, isomerised sugar (fructose) and so on'. For lactose they elaborate as 'lactose, isomerised lactose (lactulose), reduced lactose (lactitol)'. For sugar alcohols they include sorbitol, mannitol, reduced malt syrup (maltitol), reduced starch saccharides, xylitol, reduced palatinose and so on'. Tetroses are defined as obtained from glucose fermentation.

Zydis is a technology platform owned by R P Scherer (now Cardinal Health) where fast dissolving formulations are manufactured by blending and dissolving an active ingredient with a polymer, sugar and other ingredients followed by freeze drying (lyophilisation or in the context of the patent description 'sublimation'). Although some authors have proposed that freeze dried formulations are problematic and have proposed solvent extractable matrices or matrices incorporating solvent sublimation to add advantage (Gregory et al, 1983; Gole et al, 1994) the Zydis technology is still popular. Gregory et al (1983) and Gole et al (1994) discuss the use of dextrins in their (sublimed/freeze dried) delivery matrices but do not define which type of dextrin which is very confusing in view of the very different chemistries and physical properties of different dextrins. The authors do not have interests in tablet production (by compression) per se. In reality, only some dextrins would impart desirable characteristics (forming the appropriate structure and melt type characteristics) in these freeze dried matrix types whilst others would be detrimental. For example, the dextrins present in maltose syrups have a very low molecular weight and would be very different (size, shape, structure, solubility, reducing power, rheology, digestibility etc.) from dextrins produced from very limited (acid or α-amylase) hydrolysis of native starches. In fact, the only example Gregory (1983) cite is 'dextrin' (not type, source etc.) while the Gole et al (1994) application is based on (exemplified by) maltodextrin (which is generated by α-amylase but not β-amylase as previously discussed). It is apparent in these patents that the applicants do not understand the breadth of different chemical species and properties in different types of dextrins. Different dextrins have different properties and chemistries.

BRIEF DESCRIPTION OF THE INVENTION

According to the invention, there is provided a formulation, typically a pharmaceutical formulation, comprising an active agent and at least one excipient, wherein the at least one excipient comprises a β-limit dextrin.

Typically, the formulation is suitable for administration to the human or animal body.

In this specification, the terms "pharmaceutical product" and "pharmaceutical formulation" should be understood to include therapeutic and prophylactic pharmaceutical products as well as health promoting or nutritional products which include vitamins, minerals, herbal remedies, proteins, amino acids and the like and consumable products such as breath fresheners. The product could be used as a nutritional or pharmaceutical agent and may be administered on (e.g. topical on skin) or within the body by one or more route (e.g. oral, nasal, vaginal, pulmonary, rectal, intravenous, intramuscular, intraperitoneal, etc.) for its specific activity. As such, the term "active agent" should not be construed as being limited to pharmaceutically active agents, but may comprise cellular material (e.g. cells, microorganisms), genes, nutritional supplements and flavours or fragrances or the like.

In one embodiment, the active agent is a pharmaceutically active agent.

In a preferred embodiment, the β-limit dextrin is a carrier for the active agent.

Typically, the pharmaceutical formulation is a bioadhesive pharmaceutical formulation in which the -limit dextrin carrier acts as a mucoadhesive excipient. In this specification, the term "bioadhesive pharmaceutical formulation" should be understood to mean pharmaceutical formulations which are intended to deliver an active agent to a mucosal membrane of a mammalian body. In humans, such mucosal membranes include those located in the buccal cavity, intestine, the nasal cavity, the lungs and throat, the vagina, and the rectum In one embodiment, the bioadhesive pharmaceutical formulation is a buccal-melt type product, or a wafer. In another embodiment, the bioadhesive pharmaceutical formulation is a powder for use in aerosol delivery formulations, typically aerosol formulations for nasal or pulmonary delivery. The material may be solubilised/dispersed and administered accordingly (for example in the mouth as a solution or the nasal/pulmonary route as a spray/mist (or equivalence)).

In an alternative embodiment, the bioadhesive pharmaceutical formulation is a thin film, typically of the type commonly used as a carrier of breath freshener fragrances.

The invention also relates to the use of β-limit dextrin as a mucoadhesive carrier. In particular, the invention relates to the use of β-limit dextrin. as a mucoadhesive carrier in a pharmaceutical formulation. The invention also relates to the use of β-limit dextrin as a mucoadhesive carrier in non-pharmaceutical applications such as, for example, a thin-film breath freshener.

In one embodiment which is a formulation for oral delivery, the pharmaceutical formulation of the invention is a buccal melt product. Typically, the pharmaceutical formulation is in a form selected from the group comprising: particulate; capsule; tablet; freeze dried matrix; wafer; and liquid. In this specification, the term "particulate product" should be understood to include powders, granules, flakes and the like. Typically, the particulate product is derived from pulverised freeze dried matrices, granulated, roller dried, or spray dried material. Suitably the particulate product is a pharmaceutical product. In one embodiment of the invention, the particulate product is an inhalation-type product.

The invention also relates to a liquid formulation comprising an active agent, and a dispersant, wherein the dispersant comprises β-limit dextrin. Typically, the liquid formulation is a pharmaceutical formulation.

The invention also relates to the use of β-limit dextrin as an excipient in a pharmaceutical formulation.

The invention also relates to a nutritional product comprising β-limit dextrin. Suitably, the β-limit dextrin is used as an energy source. Typically, the β-limit dextrin is a main energy source in the product. This is not always the case, however, as it may be consumed in conjunction with other carbohydrates (or energy sources). In one embodiment, the nutritional product is an energy drink of the type sold under the Trade Name "Lucozade". In an alternative embodiment of the invention, the nutritional product is a confectionary product, such as, for example, a sweet or a chocolate product.

The invention also relates to the use of β-limit dextrin as an energy source in a clinical-nutritional product. In particular, the invention relates to the use of β-limit dextrin as an energy source in an energy drink.

In one embodiment, the β-limit dextrin is obtainable by hydrolysing starch with β-amylase.

This invention also relates to the use of β-limit dextrin alone as a source of energy. It may be formulated in drinks, foods, feeds and the like for this purpose.

The invention also relates to the use of β-limit dextrin as a dispersant in liquid pharmaceutical and non-pharmaceutical formulations.

The invention also relates to the formation of β-limit dextrin in situ in the formulated product where the substrate (amylose or amylopectin) is hydrolysed within the finished or near-finished product by the (added or endogenous) β-amylase.

Melt Formulations

These are rapidly disintegrating formulations which are intended to be dissolved very rapidly in the buccal cavity (mouth). Generally these formulations lack physical strength. One example of the use of the β-limit dextrins in buccal melt type products is presented in Example 1.

Use of β-limit Dextrins in Freeze Dried Matrices and Tablet (Including Melt) Type Formulations These have not been defined elsewhere. As discussed above, freeze dried matrices have been described (containing 'dextrins') but do not incorporate the use of β-limit dextrins. Furthermore, tablet formulations with melt or fast/slow/controlled release type formulations have not been described at all where β-limit dextrins have been incorporated. The unique characteristics of β-limit dextrins in freeze dried matrices and tablets are unexpected and surprisingly. Examples of the use of freeze dried matrices is presented in Example 2 and 3.

Powder Formulations Incorporating β-Limit Dextrins

These molecules can be formed from dried matrices (e.g. from pulverised freeze dried matrices or from granulated or spray dried material). We have found that active agents can be incorporated into these matrices before drying or blended together subsequently. These applications are discussed below. This material clearly has applications in tablets (above), sachets etc. and as an inhalation type (nasal/pulmonary) carrier as the material is quite 'sticky' when hydrated.

Liquid Formulations Incorporating β-Limit Dextrins

This dextrin is highly soluble. Also, because of the removal of exterior chains (of amylopectin) the product cannot retrograde (recrystallise) easily if at all from solution. This makes the product very stable in solution and appropriate as a dispersing component in liquid pharmaceutical (and non-pharmaceutical) preparations. The solutions readily form mists when sprayed making ideal carriers for pulmonary and nasal delivery.

Film Formulations Incorporating β-Limit Dextrins

Figure 1:
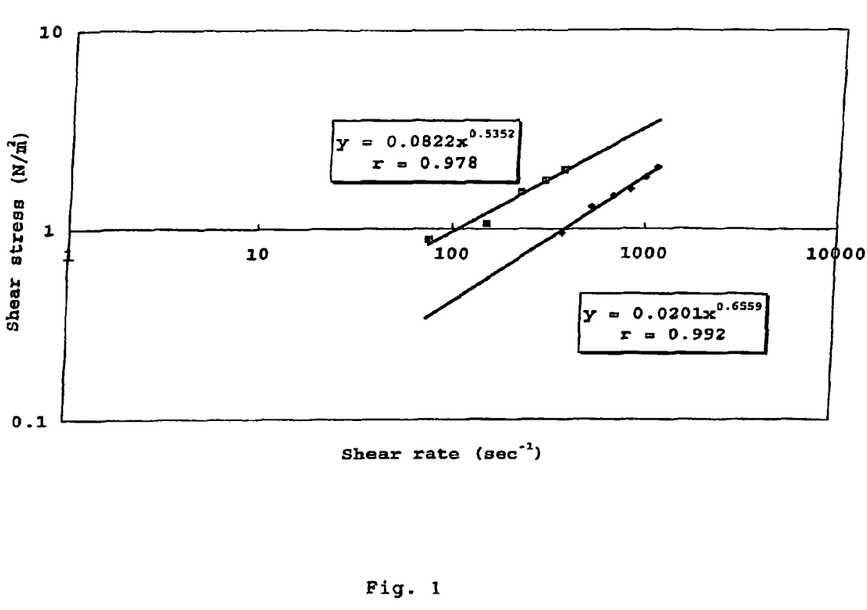

A dextrin solution incorporating active agents (as described above) forms thin film when oven dried. This makes it a suitable carrier in food, personal care or pharmaceutical preparations.

BRIEF DESCRIPTION OF THE FIGURES

The invention will be more clearly understood from the following description of some embodiment thereof, given by way of example only, with reference to the accompanying Figures in which:

FIG. 1 is a graph showing the Theological properties of glucose (bottom line) and β-limit dextrin (top line) solutions containing 1% theophylline;

FIG. 2 is a graph comparing the mucoadhesive forces (N) of tablets containing β-limit dextrin and Carbopol;

FIG. 3 is a graph comparing the mucoadhesive forces (N) of tablets containing Chitosan, Carbopol, and a placebo;

FIG. 4 is a graph comparing the mucoadhesive forces (N) of a mixture of β-limit dextrin and sodium alginate, and sodium alginate alone; and FIGS. 5 and 6 are graphs showing the dissolution properties of formulations according to the invention.

DETAILED DESCRIPTION OF THE INVENTION

β-Limit Dextrin Production

These dextrins may be produced from starches of different botanical origins and different genetic modifications, chemical, enzymatic or physical derivatives. Since all the amylose is converted to maltose, it is much more cost effective to use high amylopectin ('waxy type') starches where there is a higher proportion of amylopectin—the origin of the β-limit dextrin.

The dextrin may be produced by a number of routes and the following method does not exclude material produced by other routes nor using other sources of enzyme or processing conditions.

The dextrin is produced in conjunction with maltose from the α-glucan hydrolysis. In the method descried below, the maltose is removed by dialysis leaving pure dextrin. However, the maltose could be left in the product as an option (to impart sweetness and novel functionality).

Waxy maize starches (c. 25 g) were dissolved in 500 ml acetate buffer (0.02M, pH 4.8) at 100° C. for at least 1 hour. After cooling to room temperature, crystalline sweet potato β-amylase ($5\times10^3$ units, Sigma A-7005) was added and the mixture was thoroughly mixed. The mixture were then transferred into dialysis tubing (Visking code DTV 12000.13.000) and incubated for 36 hours at 37° C. under dialysis against the same buffer, which was renewed three times during the first 3 hours and twice afterwards. Chromatography would be a preferred industrial separation method. After the reaction had been terminated by heating the mixture for 10 mins at 100° C., the coagulated protein was removed by centrifugation, and then ethanol was added to the solution. The resulting precipitate was collected by centrifugation, dissolved in water (250 ml) and then re-precipitated by the addition of ethanol. The precipitate recovered on centrifugation was finally dissolved in water and then dried (below).

Drying Tests (Dextrin Alone)

The dextrin was dried using freeze drying and spray drying (including use of small pilot scale Büchi mini spray dryer model B-191). The spray dried material is a fine powder with good flow characteristics. The freeze dried material makes a fine lyophilised matrix. This may be milled to a powder which tends to be a little electrostatic in character. The material was also wet granulated from the dried materials which was, itself, readily tableted (below).

Dextrin Characterisation

Composition

Moisture content: depends on drying protocol (<9%)

Protein: <0.5%

Ash: <0.3%

Molecular weight: $3.1\times10^6$ $gmol^{-1}$

Solubility

| Solvent/Temperature (° C.) | Solubility (w/v, %) |
|---|---|
| Water 25° C. | 31 |
| Water 50° C. | 34 |
| 0.01M HCl (pH2) 25° C. | 33 |
| 0.01M HCl (pH2) 50° C. | 43 |
| 0.01M NaOH (pH12) 25° C. | 34 |
| 0.01M NaOH (pH12) 50° C. | 36 |

Stability (5% Solution, 25° C.)

The stability was assessed where the time for the solution to become opaque then form precipitates at different pH's was determined.

| pH | Storage stability (days) |
|---|---|
| 3 | 94 |
| 7 | 9 |
| 11 | 17 |

Molecular Characterisation

The product of β-amylase hydrolysis was analysed by gel permeation chromatography (GPC, using Sepharose CL-2B gels) according to Karkalas and Tester (1992) before and after dialysis (to remove maltose). Accordingly the retention time and molecular weight of the dextrin was smaller than the native amylopectin (with maltose present prior to dialysis). This confirms that the native amylopectin molecules were selectively hydrolyzed.

Rheological Properties

To prove that the rheological properties of a drug in solution with a sugar (glucose) or the β-limit dextrin are different in terms of interactions the following experiment was conducted.

Samples of theophylline and either glucose or the β-limit dextrin were dispersed in water (to give a concentration of 1% theophylline, w/w and either 1% with respect to glucose or beta-limit dextrin, w/w) within sealed screw capped tubes. These were sealed and mixed and kept in a 25° C. water bath. The viscosity was immediately determined using a Brookfield DV-III Viscometer (Brookfield Engineering Laboratories, INC., USA) fitted with a cone and spindle CP-40 system (2.4 cm dimension and 0.8° angle) with a thermostatically controlled temperature of 25° C. A silicon viscosity standard (96.2 mPas at 25° C.) from Brookfield was used for calibration. The results are shown in FIG. 1.

Enzyme Digest with or without Dialysis to Remove Maltose.

The properties of formulations containing the dextrin which have none, some or all of the maltose removed (howsoever) differ in their properties. These are also considered below.

Energy Product

The solubility of the dextrin and its high molecular weight make it very valuable as a component of drinks to provide a slow release of energy.

Applications

EXAMPLES

1. Melting Formulations

β-limit dextrin was wet-granulated as described later in this application. Two formulations were prepared where the Carbopol formulation was used as a standard as it has well established mucoadhesive properties.

Formulation:
20% β-limit dextrin
6% PVP 44000
1% Magnesium stearate
73% Spray-dried lactose Formulation:
20% Carbopol 934
6% PVP 44000
1% Magnesium stearate
73% Spray-dried lactose Tablets were made using a single-punch tablet press (Manesty F3, Liverpool, UK) and 6 mm diameter flat punches. β-limit dextrin formulation produced thicker tablets due to the lower bulk density of the mixture. The tablet's crushing strength was measured using a tablet hardness tester (Model TBH28, Erweka, Heusenstamm, Germany). At compaction pressure of 35N, crushing strength of 45N was obtained for β-limit dextrin formulation whereas the value for Carbopol formulation was 160N.

Mucoadhesion test was carried out in vitro using double strength nutrient agar coated with a 5% solution of porcine mucin over the surface. Measurements were made with a Texture Analyser (TA-XT2i, Stable Micro Systems, Surrey, UK) by applying a force of 0.15N and a contact time of 10 minutes. The adhesive forces obtained are shown in FIG. 2.

Figure 2:
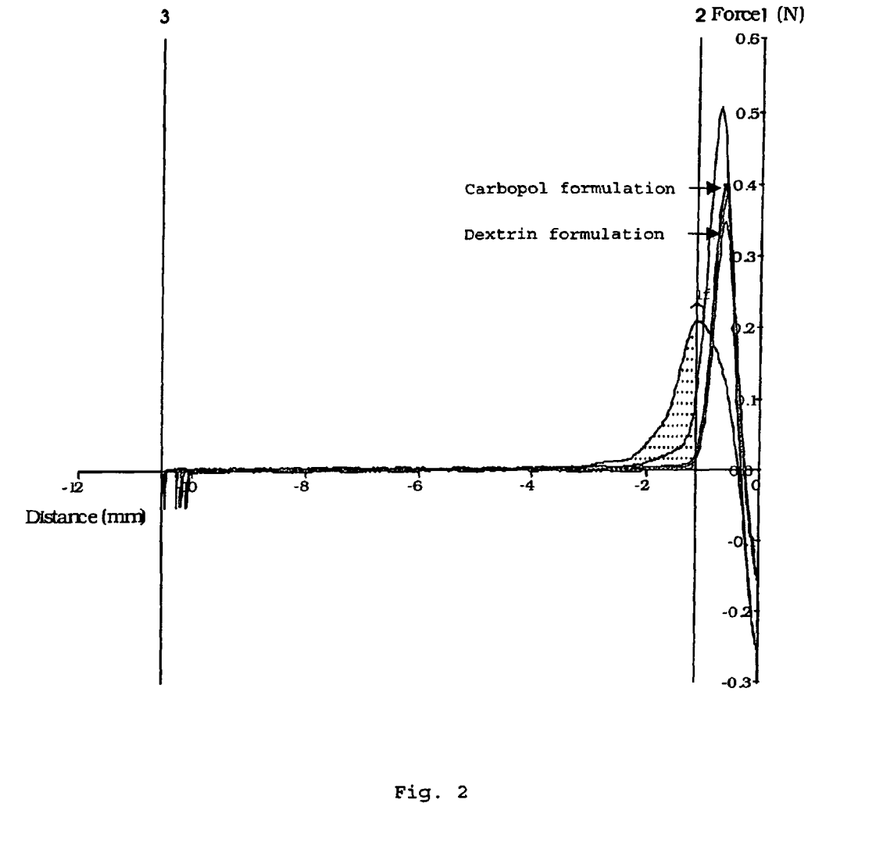

As can be seen in FIG. 2, the mucoadhesive force of the Carbopol formulation was about 0.40N on average, with the average value for the β-limit dextrin formulation about the same (0.38N). Under these conditions therefore the mucoadhesive force of β-limit dextrin was very similar to the Carbopol.

The contact force was then increased to 0.25N. The proportion of β-limit dextrin was increased to 30% and this was found to be the optimal concentration. Three formulations were prepared as follow:

Formulation:
30% β-limit dextrin
6%. PVP 44000
1% Magnesium stearate
63% Spray-dried lactose Formulation:
30% Carbopol 934
6% PVP 44000
1% Magnesium stearate
63% Spray-dried lactose Formulation:
30% Chitosan
6% PVP 44000
1% Magnesium stearate
63% Spray-dried lactose A 'placebo' tablet was also prepared that contained no known mucoadhesion. Mucoadhesion force was measured as mentioned above with contact time of 10 minutes. The average mucoadhesive forces are 0.097N, 0.245N and 0.450N for tablets containing placebo, chitosan and Carbopol respectively comparing to the value of 0.464N for β-limit dextrin.

Figure 3:
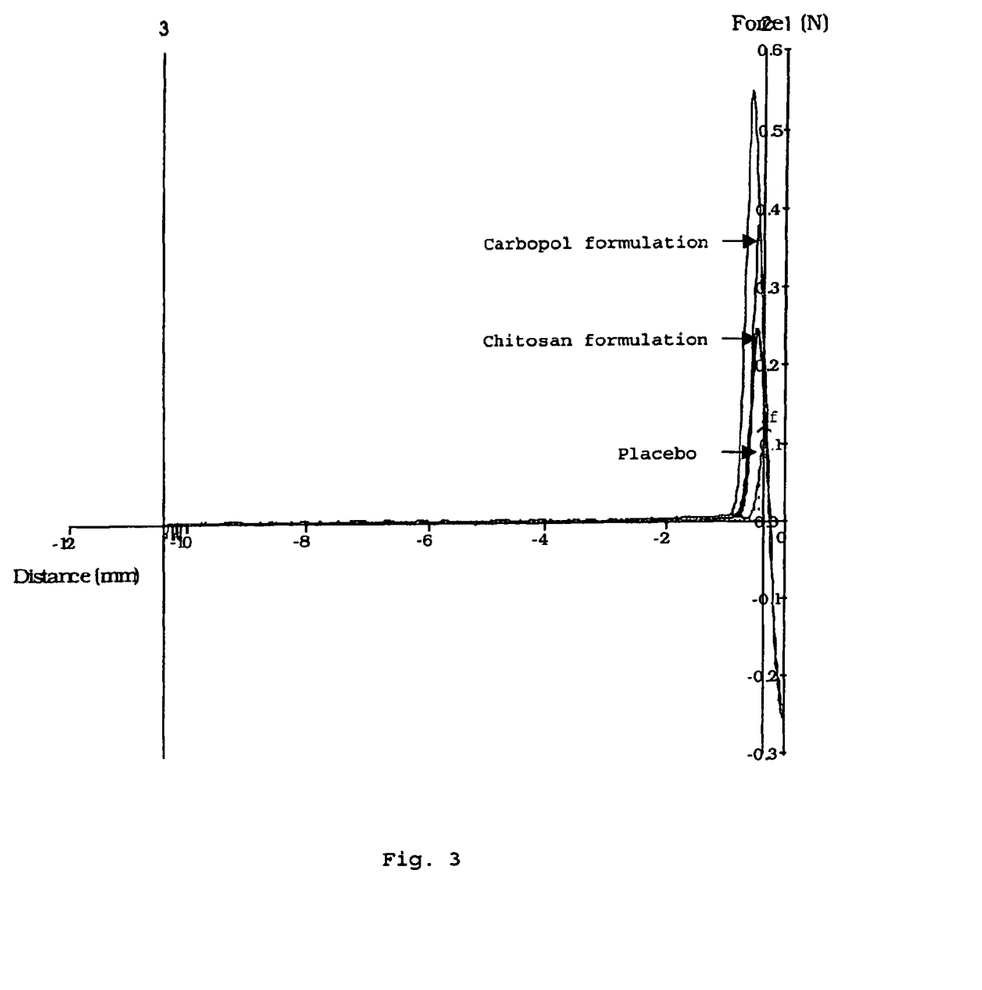

The results (see FIG. 3) demonstrate that the β-limit dextrin does have significant mucoadhesive properties.

The mucoadhesive property of β-limit dextrin can be improved by addition of other polysaccharides (e.g. sodium alginate). Two formulations were prepared as follow:

| Ingredients(mg/tablet) | A | B |
|---|---|---|
| β-limit dextrin | 20 | — |
| Sodium alginate | 10 | 30 |
| PVP 44 000 | 6 | 6 |
| Magnesium stearate | 1 | 1 |
| Spray-dried lactose | 63 | 63 |

Figure 4:
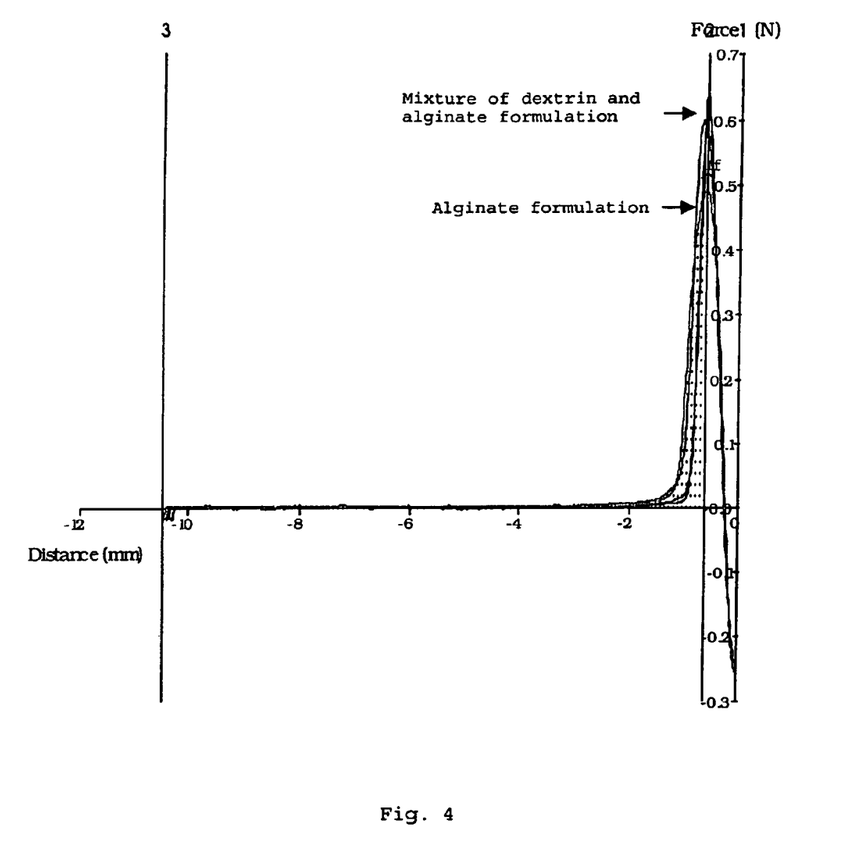

The mucoadhesive forces measured as described above are 0.629N and 0.544N for formulation A and formulation B respectively, although 0.464N was obtained without addition of sodium alginate for the previous formulation (Page 24). The above results (see also FIG. 4) show that the addition of alginate does increase the mucoadhesive force of β-limit dextrin significantly.

2. Dried Matrices

Solutions/suspensions containing the dextrin and theophylline (e.g. 10% with respect to the dextrin and 0.1% with respect to theophylline) were freeze-dried where easily hydratable matrices were formed. These melt type formulations can also be milled to produce fine powders.

The matrices 'melted' or rather dissolved and dispersed exceedingly easily when water came into contact with them. It is evident that freeze-dried products could be made from this material.

3. Tablet Formulations

It was found that the dextrin could be tableted directly to form products with different drugs. The following examples exemplify this.

a. Direct Compression

β-limit dextrin was prepared from waxy maize starch and was spray dried to form a fine powder.

b. Granulation

Samples (15 g) of the β-limit dextrin (dried by freeze drying) was wet massed with 5 ml water using an FP296 mixer (Kenwood Ltd, UK). Granules were then spread evenly over a drying tray and dried overnight at 60° C. Dried granules were passed through a 300 μm mesh to produce a free-flowing powder.

Two formulations were produced using the same water-soluble drug but different types of additional tabletting excipient since the tablet release matrix (first) formulation was not easily tabletable with drug alone (as friable tablets were produced). Each formulation was then tested using a standard USP II paddle dissolution apparatus (ST-7 model, Caleva Ltd, UK) at 37° C. in 1000 ml water ($\lambda_{max}$ propranolol.HCl=298 nm).

Formulation 1. β-Limit Dextrin, Hydrophilic Excipient and Tablet Release Formulation
Formulation:
40% β-limit dextrin
20% Microcrystalline cellulose (Avicel 101)
20% Lactose
20% Propranolol.HCl The formulation was mixed for 30 minutes using an orbital Turbula™ mixer (Glen-Creston Ltd, Middlesex, UK). The resultant mixture was then tableted with a 7.95 mm concave punch and die set using an E2 single punch tablet press (BWI-Manesty Ltd, Liverpool, UK).

Tablet properties made according to hydrophilic tablet. Formulation

| No. | Weight (mg) | Thickness (mm) | Hardness (N) | Diameter (mm) |
|---|---|---|---|---|
| 1 | 194.9 | 3.99 | 36 | 7.95 |
| 2 | 201.6 | 4.09 | 40 | 7.94 |
| 3 | 181.6 | 3.79 | 28 | 7.93 |
| 4 | 201.0 | 4.06 | 46 | 7.93 |
| 5 | 179.6 | 3.75 | 25 | 7.93 |
| 6 | 190.7 | 3.95 | 32 | 7.96 |
| 7 | 177.9 | 3.73 | 32 | 7.94 |
| 8 | 194.3 | 4.00 | 24 | 7.94 |
| Mean | 190.2± | 3.92± | 33 ± | 7.94 |
| SD | 9.4 | 0.14 | 7 | 0.01 |

Figure 5:
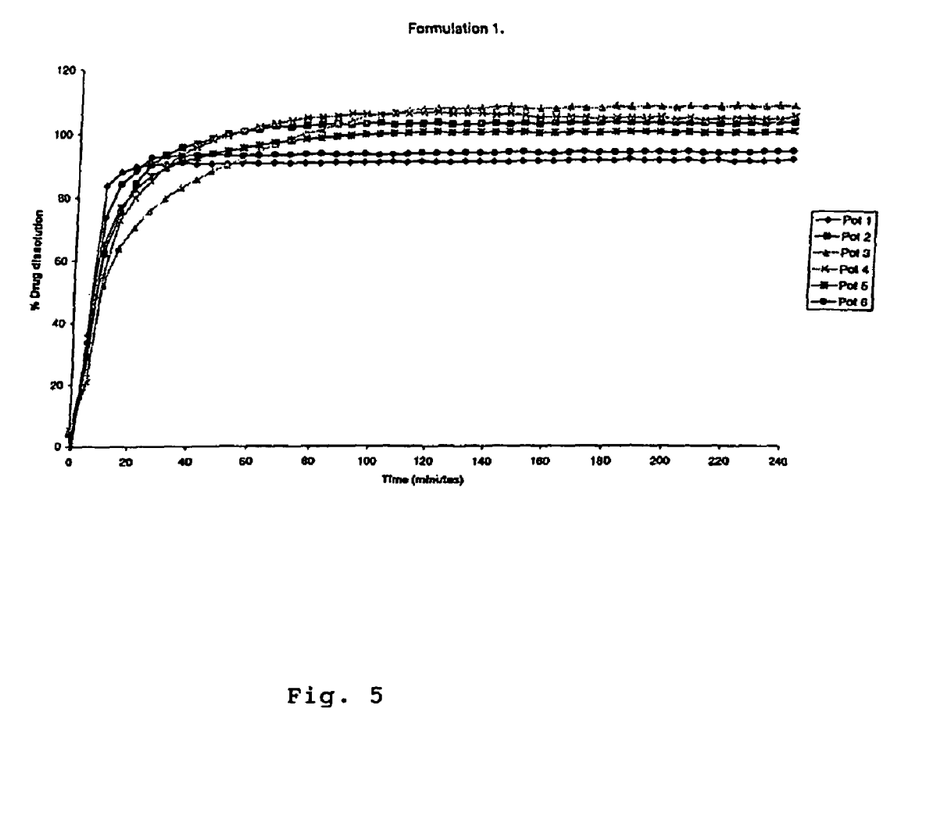

The dissolution properties of the tablets are shown in FIG. 5.

Formulation 2. β-Limit Dextrin, Hydrophobic Excipient and Tablet Release Formulation
Formulation:
50% β-limit dextrin
25% Emcompress® (Dibasic calcium phosphate)
25% Propranolol.HCl The components were mixed and compressed as with the previous formulation (1).

Tablet properties made according to hydrophobic tablet formulation

| No. | Weight (mg) | Thickness (mm) | Hardness (N) | Diameter (mm) |
|---|---|---|---|---|
| 1 | 205.0 | 3.91 | <10 | 7.94 |
| 2 | 192.9 | 3.72 | <10 | 7.94 |
| 3 | 197.4 | 3.85 | <10 | 7.94 |
| 4 | 199.2 | 3.78 | <10 | 7.94 |
| 5 | 199.9 | 3.76 | <10 | 7.96 |
| 6 | 194.0 | 3.74 | <10 | 7.94 |
| 7 | 193.7 | 3.65 | <10 | 7.96 |
| 8 | 197.4 | 3.83 | <10 | 7.97 |
| Mean | 197.4± | 3.78± | <10 | 7.94 |
| SD | 4.0 | 0.08 | | 0.01 |

Figure 6:
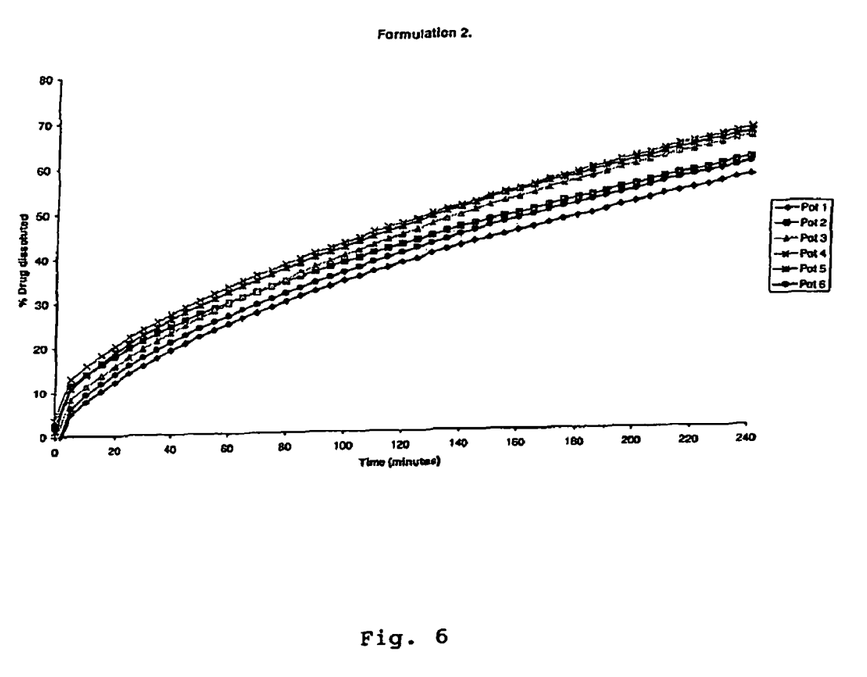

The dissolution properties of the tablets are shown in FIG. 6.

Better weight uniformity is obtained indicative of improved powder flow. Low hardness may be improved by adding a compression binding agent.

4. Powder Formulations

These may be made from milling dried matrices (e.g. '2'). However, powders can also be made directly by for example spray drying.

Solutions containing the dextrin and theophylline (e.g. 10% with respect to the dextrin and 0.1% with respect to theophylline) were spray dried where very fine powders were prepared that disperse very easily upon hydration. These may be tableted (see above) or utilised in sachet type formulations. It is anticipated that pulmonary type delivery products could be made from small particles comparable or smaller than dimensions present in these powders.

5. Liquid Formulations

The β-limit dextrin was dissolved in water (for example a 10% solution) with theophylline (for example 0.1%). The solution was found to be very stable at room temperature and could be used as a liquid formulation for oral delivery of drugs and for parenteral administration.

Liquid formulations were also made with the dextrin alone. It is clear that the stability of the dextrin makes it valuable as a provider of energy in appropriate nutritional products. The material will have a slower hydrolysis profile with for example α-amylase compared to maltodextrin because of its higher molecular weight. Spray mists were made with the solutions using a variety of devices and support the application in nasal/pulmonary applications.

6. Film Formulation

β-Limit dextrin was dissolved in deionised water, to which vitamin A solution (1 mg/ml) was added to give final concentration of 1% for β-Limit dextrin. Film was obtained after convection-oven drying the mixture in a foil tray at 30, 40 or 50° C. overnight.

7. Enhancement of Drug Solubility

It was noted that rather surprisingly the β-limit dextrin could facilitate the dissolution of drugs. There are many potential applications with respect to dispersing and solubilising insoluble compounds. The following example indicates that this is so.

Drug interaction and stability with β-limit dextrin in solution

| Drugs (1%) | Water | β-limit dextrin (5%) | β-limit dextrin (10%) |
|---|---|---|---|
| Ascorbic acid | Dissolved | Dissolved | Dissolved |
| Glucose | Dissolved | Dissolved | Dissolved |
| Theophylline | Not suspended | Suspended | Suspended |
| Aspirin | Not suspended | Suspended | Suspended |

8. Dialysis

It is also apparent that the material could be potentially used for intra-peritoneal dialysis if a low osmotic α-glucan is required. The product would potentially fulfil the need in this area provided by oligosaccharide type products like 'icodextrin' produced by ML Laboratories. The following example indicates that this is so.

The osmolality of β-limit dextrin solution (5%) was measured using an advanced 3300 crysocopic osmometer which was pre-calibrated with 0.9% aqueous sodium chloride solution. Maltodextrin (Maldex 150BB, Amylum) was used to act as a control. The results are presented as follow.

The $COP_{10K}$ (the measured osmotic pressure of the solution across a membrane with a pore size of 10,000 Daltons) of the same sample solutions was also measured using an Osmomat 030 colloid osmotic pressure osmometer. A 6% haes solution was used to calibrate the pore size as it varies depending on the age of the membrane. The $COP_{10K}$ results are given as follow.

| Samples(5%) | Osmolality (Milliosmol/kg) | COP10K (mmHg) |
|---|---|---|
| β-limit dextrin | 16.2 | 3.9 |
| Maltodextrin | 43.7 | 20.9 |

9. Adhesions

Similarly to the icodextrin product discussed above, it is anticipated that the material could function to prevent tissue adhesion.

10. Drink Formulations

Drinks were prepared from 0-20% β-limit dextrin and flavourings (<0.1%). The product is not sweet. Hence, sweetening was added in (a) the form of sugar (sucrose, 5-10%) or (b) aspartame (<0.1*) plus flavours. The products had a much better organoleptic property and could be used as the basis of formulated energy products.

The invention is not limited to the embodiments hereinbefore described which may be varied in detail without departing from the spirit of the invention.

References

Ammeraal, R. and Friedman, R. (1995) Beta-limit dextrin from dull waxy starch. UK Patent 2,291,882.

Ammeraal, R. and Friedman, R. (1996) Beta-limit dextrin from dull waxy starch. U.S. Pat. No. 5,482,560.

Aten, J., Dijkstra, P., Kaper, F. S., Reinders, M. A. and Suvee, A. J. (1986) Preparation of beta-limit dextrin containing starch hydrolysates—from gelatinised starch with beta-amylase then alpha-amylase. NL 86937 A then EP 242913 A and U.S. Pat. No. 4,780,149 A. Gole, D. J., Levinson, R. S., Carbone, J. and Davis, D. J. (1994) Delivery matrices prepared by solid-state dissolution. U.S. Pat. No. 5,330,763

Gregory, G. K. E., Peach, J. M. and Du Mayne, J. D. (1983) Articles for carrying chemicals. U.S. Pat. No. 4,371,516.

Kaper, F. S., Aten, J., Reinders, M. O., Dijkstra, P. and Suvee, A. J. (1987) A method of making and applying beta-limit dextrin containing starch hydrolysates. EP 87200685 EP 0,242,913 A2 (then U.S. Pat. No. 4,780,149).

Karkalas, J. and Tester, R. F. (1992). Continuous enzymic determinations of eluates from gel-chromatographic columns. Journal of Cereal Science 15, 175-180.

Makino, T., Yamada, M. and Kikuta, J-I (1993) Fast dissolving tablet and its production. European Patent 0 553 777 A2 and U.S. Pat. No. 5,720,974.

Ohno, Y., Makino, T., Kikutu, J. (1999) Solid pharmaceutical preparation with improved buccal disintegrability and/or dissolubility. U.S. Pat. No. 5,958,453.

Outtrup, H. and Norman, B. E. (1990) Beta-amylase enzyme product, preparation and use thereof. U.S. Pat. No. 4,970,158.

Uekama, K., Yoshiyuki, T., Ijitsu, T. and Yamada, T. (1989) Sustained release drug preparation. U.S. Pat. No. 4,869,904.

Yoshida, T., Ishige, Y., Matsudaira, M. and Takahashi, T. (1989) Branched dextrin production and compositions containing same. U.S. Pat. No. 4,840,807.

The invention claimed is:

1. A bioadhesive pharmaceutical formulation comprising an active agent and a mucoadhesive carrier for the active agent, wherein the mucoadhesive carrier comprises a β-limit dextrin which is obtained by hydrolyzing waxy starch, and said formulation is a buccal melt product comprising a freeze-dried matrix, wherein the buccal melt product is a wafer.

2. A bioadhesive pharmaceutical formulation as claimed in claim 1 in which the active agent is a pharmaceutically active agent.

3. A bioadhesive pharmaceutical formulation as claimed in claim 1 which is a thin film.

4. A bioadhesive pharmaceutical formulation as claimed in claim 1 further including at least one carbohydrate.

5. A bioadhesive pharmaceutical formulation as claimed in claim 4 in which the at least one carbohydrate is a polysaccharide.

6. A bioadhesive pharmaceutical formulation as claimed in claim 4 in which the at least one carbohydrate is selected from the group consisting of: alginate; pectin; and derivatives of alginate and pectin.

7. A bioadhesive pharmaceutical formulation as claimed in claim 6 in which the alginate comprises between 1 and 50% of the formulation (w/w).

8. A bioadhesive pharmaceutical formulation as claimed in claim 7 in which the alginate comprises between 10 and 30% of the formulation (w/w).

9. A bioadhesive pharmaceutical formulation as claimed in claim 1 in which the active agent is a breath freshener.

10. A bioadhesive pharmaceutical formulation comprising an active agent and a mucoadhesive carrier for the active agent, wherein the mucoadhesive carrier comprises a β-limit dextrin which is obtained by hydrolyzing waxy starch, and said formulation is a buccal melt product comprising a freeze-dried matrix, wherein the buccal melt product is a wafer and wherein the waxy starch comprises greater than 70% amylopectin.

11. A bioadhesive pharmaceutical formulation as claimed in claim 10 in which the active agent is a breath freshener.

12. A bioadhesive pharmaceutical formulation as claimed in claim 10 in which the active agent is a pharmaceutically active agent.

13. A bioadhesive pharmaceutical formulation as claimed in claim 10 further including at least one carbohydrate.

14. A bioadhesive pharmaceutical formulation as claimed in claim 13 in which the at least one carbohydrate is a polysaccharide.

15. A bioadhesive pharmaceutical formulation as claimed in claim 13 in which the at least one carbohydrate is selected from the group consisting of: alginate; pectin; and derivatives of alginate and pectin.

16. A bioadhesive pharmaceutical formulation as claimed in claim 15 in which the alginate comprises between 1 and 50% of the formulation (w/w).

* * * * *